United States Patent [19]
Yager

[11] Patent Number: 5,932,418
[45] Date of Patent: Aug. 3, 1999

[54] FISH EMBRYO SCREENING TEST FOR GENOTOXIC AGENTS USING THREE DIFFERENT DEVELOPMENTAL LIFE STAGES

[75] Inventor: Thomas Dean Yager, Ontario, Canada

[73] Assignee: Naiad Systems, Inc., Ontario, Canada

[21] Appl. No.: 08/832,786

[22] Filed: Apr. 4, 1997

Related U.S. Application Data

[60] Provisional application No. 60/015,034, Apr. 8, 1996.

[51] Int. Cl.$^6$ ........................................................ C12Q 1/68
[52] U.S. Cl. .................................. 435/6; 435/1.2; 436/63; 436/94; 424/9.2
[58] Field of Search ........................... 435/6, 1.2; 436/94, 436/63; 424/9.2

[56] References Cited

U.S. PATENT DOCUMENTS

| | | | |
|---|---|---|---|
| 4,153,676 | 5/1979 | Jelinek et al. | 424/9 |
| 4,346,070 | 8/1982 | Johnson | 424/9 |
| 5,565,187 | 10/1996 | Zikria et al. | 424/9.6 |

OTHER PUBLICATIONS

Kocan RM and ML Landolt, 1990, Use of herring embryos for in situ and in vitro monitoring of marine pollution; in: "In Situ Evaluations of Biological Hazards of Environmental Pollutants," by S.S. Sandau et al. Eds., Plenum Press, New York, pp. 49–60.

Klymkowsky MW and J Hanken, 1991, Whole mount staining of Xenopus and other vertebrates, Meth. Cell Biol. 36, 419–441.

Patel NH, E Martin–Blanco, KG Coleman, SJ Poole, MC Ellis, TB Kornberg, and CS Goodman, 1988, Expression of engrailed proteins in Arthropods, Annelids, and Chordates; Cell 58, 955–968.

Thiry M., 1992, Highly sensitive immunodetection of DNA on sections with exogenous terminal deoxynucleotidyl transferase and non–isotopic nucleotide analogues; J. Histochem. Cytochem. 40: 419–441.

Gavrieli Y, Sherman Y and Ben–Sasson SA; 1992, Identification of programmed cell death in situ–via specific labeling of nuclear DNA fragmentation; J. Cell Biol. 119:493–501.

Lange M, Gebauer W, Markl J and Nagel R, 1995, Comparison of testing acute toxicity on embryo of Zebrafish, Brachydanio rerio and RTG–2 cytotoxicity as possible alternatives to the acute fish test; Chemosphere 30(11): 2087–2102.

Longwell AC and Hughes JB; 1980, Cytologic, cytogenetic, and developmental state of Atlantic mackerel eggs from sea surface waters of the New York Bight, and prospects for biological effects monitoring with ichthyoplankton; Rapp-.P.–v.Reun.Cons.int. Explor.Mer,179:275–291.

Liguori VM and Landolt ML, 1985, Anaphase aberrations: an in vivo measure of genotoxicity; in: "Short–Term Bioassays in the Analysis of Complex Environmental Mixtures IV," by Waters MD et al (eds.), Plenum Press, New York, pp. 87–98.

*Primary Examiner*—Kenneth R. Horlick

[57] ABSTRACT

A sensitive bioassay, consisting of two assay techniques applied to embryos of a teleost (bony fish), is utilized in testing for genotoxic agents. The assay allows genotoxic effects to be scored at three different embryo life-stages: (1) before mid-blastula transition (MBT), (2) after MBT, and (3) after mid-gastrula transition. Each embryo life-stage displays different ranges of sensitivity to genotoxic agents. In the first assay technique, embryos are stained for chromosome morphology and then examined, in the form of "flattened whole mounts", by epifluorescence microscopy, for cytogenetic defects. In the second assay technique, embryos are stained for fragmentation of DNA that is associated with apoptosis, and then a flattened whole mount of the embryo is examined. If the result of the cytogenetic assay is negative (with few or none of the cells in the embryo showing cytogenetic defects), then the apoptosis assay can be performed. The bioassay provides quantifiable biomarkers as measures of the sublethal effects of different chemicals or types of radiation. The bioassay would be useful to cost-effectively screen large numbers of samples, including complex environmental samples, and could be useful in identifying compounds responsible for toxicity.

24 Claims, 4 Drawing Sheets

FISH EMBRYO SCREENING TEST FOR GENOTOXIC AGENTS USING THREE DIFFERENT DEVELOPMENTAL LIFE STAGES

This application claims the benefit of U.S. Provisional Application Ser. No. 60/015,034, filed Apr. 8, 1996.

BACKGROUND—FIELD OF INVENTION

This application relates to a test which employs embryos of teleosts (bony fish) to screen aqueous samples for the presence of genotoxic compounds. With this invention, the following aqueous samples of interest can be tested: aqueous chemical solutions, aqueous chemical mixtures, aqueous chemical suspensions, and aqueous solutions under the influence of electromagnetic or particulate radiation.

BACKGROUND KNOWLEDGE AND DESCRIPTION OF PRIOR ART

The present invention teaches a method for detecting and quantifying, in embryos of teleosts (bony fish), two classes of phenotypes: (1) fragmentation of DNA that is indicative of apoptosis, and (2) a broad range of cytogenetic defects. These classes of phenotypes can be produced by exposure to a deleterious chemical substance in the medium which bathes the embryos; and also by exposure to aqueous solutions under the influence of particulate or electromagentic radiation.

The present invention relies to some extent on background knowledge from the field of Developmental Biology. It also bears some relation to prior art in the fields of Pharmaceutical Testing and Environmental Testing. Because these three fields display very little overlap, they will now be reviewed separately.

1. Background Knowledge in the Field of Developmental Biology

1a. Three Embryonic Life Stages

The present invention is derived ultimately from a scientific discovery, by the inventor, that the embryo of the zebrafish (*Danio rerio*) displays three different levels of ability to cope with exposure to genotoxic compounds or stimuli, depending on its stage of development. In particular, the zebrafish embryo displays a profound increase in coping ability at the mid-blastula transition (MBT; 10th–12th cleavage division), and displays a second profound increase in coping ability at the midgastrula transition (MGT; 15th–16th cell-cycle). By an argument that is based on evolutionary conservation, it is reasonable to hypothesize that similar developmental shifts should be displayed by other teleost embryos.

The context for this discovery by the inventor was provided in part, but only in part, by three papers in the scientific literature which describe the early developmental stages of two teleosts, zebrafish and the mummichog killifish (*Fundulus heteroclitus*.) See Trinkaus J P, Development 1992, Suppl. 75–80 (1992); Kane D A et al. Nature 360, 735–737 (1992); Kane D A & Kimmel C B, Development 119, 447–456 (1993); Zamir E et al Molec. Cell Biol. 17: 529–536 (1997). These were publications to first describe the midblastula transition (MBT).

1b. Mid-Blastula Transition (MBT)

The MBT is a fundamental developmental milestone in the life-cycle of teleosts (and also in other lower vertebrates and invertebrates). In zebrafish, it occurs around 10th cleavage division, and is associated with a general lengthening of the cell-cycle, and with the appearance of different subpopulations of embryonic cells which display different cell-cycle periods.

The inventor hypothesized that the mid-blastula transition might also be associated with an increased capability of embryonic cells to cope with genotoxic insults. By experiments in which zebrafish embryos were exposed to inhibitors of different elementary cell-cycle processes, this was found to be the case. Before the mid-blastula transition, cells of the zebrafish embryo are unable to alter the progression of the cell-cycle, when exposed to inhibitors of elementary cell-cycle processes. Consequently, such exposure is lethal. After the mid-blastula transition, cells of the zebrafish embryo become capable of survival either by arresting the cell-cycle, or by entering an "adaptive" mode of replication, in response to treatment with these agents. This aspect of the inventor's discovery is referenced in a published abstract (Ikegami R, Hunter P, Rivera A & Yager T D. Apr. 24–26, 1996. Zebrafish Development and Genetics. Cold Spring Harbor, N.Y.) and is diagrammed in FIG. 1.

1c. Mid-Gastrula Transition (MGT)

The inventor unexpectedly discovered a second developmentally-timed increase in the capability of the zebrafish embryo to cope with genotoxic insults. Around the mid-gastrula stage (approximately 15th cell-cycle), cells of the zebrafish embryo become capable of undergoing apoptosis (programmed cell death) in response to treatment with inhibitors of elementary cell-cycle processes. Although this type of biological response is well-known for cultured lines of adult (somatic) mammalian cells, it apparently has never been described before for cells of an early embryo. This aspect of the inventor's discovery is referenced in a published abstract (Ikegami R, Hunter P, Rivera A & Yager T D. Apr. 24–26, 1996. Zebrafish Development and Genetics. Cold Spring Harbor, N.Y.) and is diagrammed in FIG. 1.

1d. Utility of Three Life-Stages for Genotoxicity Testing

Due to the inventor's discovery, it is now possible to precisely describe a developmental time-course by which the zebrafish embryo acquires successively greater and qualititatively distinct abilities to cope with genotoxic stress (FIG. 1). With the knowledge of this developmental time-course, it accordingly becomes possible to specify a series of time-points for treatment with a suspected genotoxic agent, which allows three different classes of phenotypes to be sampled or probed. This level of control or specification of the classes of phenotypes to be probed—especially the class of apoptosis-related phenotypes—was not anticipated or obvious from prior knowledge in the field of developmental biology.

In particular, a suspected genotoxic agent can be applied at the following three life-stages.

(i) Before mid-blastula transition, when many cell-cycle checkpoints are inoperative. If a test medium is inert, then the cells of the embryo will proceed through the phases of the cell cycle and will appear normal as defined and described in a standard cell biology textbook. However, if an embryo is exposed to a test medium which is not inert, but rather which contains an agent that blocks an elementary step in the cell cycle, then because of a lack of cell-cycle checkpoints, individual cells of the embryo will attempt to proceed beyond the block. Gross defects in nuclear and chromososmal structure will result, which are easily observed under the microscope and which are often lethal.

(ii) After MBT but before mid-gastrula transition, when cell-cycle checkpoints are operative but before the capability for apoptosis has appeared. If the test medium is inert, then normal progression through the cell cycle will occur. However, if the embryo is exposed to a chemical agent which interferes with the operation or progression of cell-cycle, the cells of the embryo will arrest. This arrest will be observable at the level of the whole embryo, and also at the level of individual nuclei.

(iii) After mid-gastrula transition, when the embryo is capable to undergo apoptosis. If the test medium is inert, the cells of the embryo will appear normal. However, if the test medium contains a genotoxic agent, a proportion of the cells of the embryo will enter into a state of apoptosis, in direct proportion to the toxicity of the agent.

1e. Whole-Mount Methods in Developmental Biology

The present invention uses a modification of the "whole mount" sample preparation method. Therefore, it is appropriate to review the history of whole-mount methods, which were developed in the field of Developmental Biology. In a whole-mount assay, an embryo is prepared for microscopy without sectioning. See Klymkowsky, M. W. & Hanken, J. Meth. Cell Biol. 36, 419–441 (1991) and prior art cited in Table I below. When applied to vertebrate embryos, the conventional whole-mount procedure produces a specimen which is several hundred microns thick. It is impossible to image different cell layers in a conventional whole-mount of a vertebrate embryo without confocal microscopy.

The "flattened whole mount" procedure described in this invention is a novel modification of the conventional whole mount prcedure, which addresses this fundamental limitation. The principal advantage of a flattened whole-mount, especially as applied to a vertebrate embryo, is as follows. When a deyolked embryo is flattened under a coverslip, this produces a section which is only about 5–20 micrometers thick in the z dimension. This is 10 to 40 times thinner than a conventional whole-mount, and permits imaging near the Rayleigh limit of spatial resolution. This can be achieved even with conventional (non-confocal) epifluorescence microscopy using high numerical aperature (NA) plan-field objectives. When a flattened whole-mount is prepared carefully, information about different cell-layers within the embryo will be preserved. For example, with gastrula-stage zebrafish embryos, one can resolve the three known cell layers (the superficial "enveloping" layer, the middle "deep" layer, and the innermost "yolk syncytial" layer).

To achieve even higher spatial resolution, and also to reconstruct the different layers of the flattened whole-mount as a virtual object in three dimensions, it is possible to conduct a tomographic (serial-section) reconstruction, using standard methods. See Shaw P J in "Electronic Light Microscopy" (ed D Shotton), Wiley-Liss, New York (1993). A key variable is the number of sectioning planes (N) to use in collecting the raw data. This is given approximately by the ratio of the thickness (T) of the flattened whole mount, to the depth of focus of an individual plane (D):

$$N = T/D \tag{1}$$

The depth of focus (D) of a microscope objective is defined to be the vertical distance (along the optical axis) for which the specimen "plane" will have acceptable focus. It can be estimated by the following equation:

$$D = \lambda \sqrt{(n^2 - NA^2)/NA^2} \tag{2}$$

where $\lambda$=wavelength of light, n=refractive index, and NA=numerical aperture. See Delly J D. Photography Through the Microscope, 9th Edition. Easman Kodak, Rochester, N.Y. (1988). For a typical 40× objective (for example, Zeiss plan-Neofluar NA=0.75) the depth of focus for blue light of wavelength $\lambda$=400 nm will be approximately 600 nm. Thus approximately 10–40 sections should be required for tomographic reconstruction of a flattened whole-mount.

2. Prior Art in the Field of Pharmaceutical Testing: Apoptosis Assays

Apoptosis is a stereotypic cell-death process, characterized by cell-surface blebbing, fragmentation of cell nuclei and DNA, and the absence of inflammation of surrounding tissues. It can be induced by a broad variety of genotoxic agents. In the field of pharmaceutical testing, considerable effort has been spent developing bioassays to score for apoptosis. The driving force for this has been the desire to screen for chemotherapeutic agents which may selectively induce apoptosis in cells which have undergone genetic changes leading to malignancy. See Williams G T, Cell 65, 1097–1098 (1991); Fisher D E, Cell 78, 539–542 (1994); Darzynkiewicz Z, J. Cell. Biochem. 58, 151–159 (1995); Danheiser S L Genetic Engineering News 16 (2), 1,9,26 (1996). In the pharmaceutical context, assays for apoptosis have been performed either in cultured cell lines, or in live mice.

2a. Assays in Cultured Cell Lines

Nearly all mammalian cell lines will undergo apoptosis, at least under some conditions. However, in general two types of cell lines have been used most widely. (i) One general strategy has been to use an immortalized cancer cell line, for example human promyelocytic leukemia HL-60 cells, because chemotherapeutic treatments are most often intended to target cancerous cells. See Gorczyca et al. Cancer Research 53, 3186–3192 (1993). (ii) Another general strategy has been to use immature thymocytes (pre-B and pre-T cells), which may be sensitized for apoptosis because of the negative-selection process which occurs during maturation of the immune system. See Evans D L & Dive C., Cancer Research 53, 2133–2139 (1993).

Limitations. Virtually all apoptosis assays that are based on mammalian cell-culture suffer from the following major shortcomings. (1) The genetic integrity of the cell lines has been compromised either by their derivation from a tumor, or by multiple serial passage. See Biedler J L. in Fogh J (ed) "Human Tumour Cells in Vitro" New York, Academic Press (1976); Prouty S M et al. Oncogene 8, 899–907 (1993). Typically, cells become karyotypically abnormal upon repeated passage. (2) Because of sustained genetic damage, the cell lines may behave abnormally with respect to many genetically-determined properties such as cell-cycling or apoptosis. (3) It is not possible, with existing mammalian cell culture systems, to compare the effects of a chemical agent under different developmental life-stages, in which cell-cycle checkpoints are either active or inactive. This is because all established cell lines display only the "adult" (somatic) type of cell-cycle, and never the "embryonic" form of the cell cycle. (4) The apoptosis responses which are observed may be misleading or irrelevant to the normal state of cells in the intact animal, because of the poorly-understood requirements for growth factors. It has been shown that absence or imbalance of growth factors will lead to apoptosis as an artifact. See Ishizaki Y. et al. Molec. Biol. Cell 6, 1443–1458. (1996). (5). Finally, mammalian cell culture work is prohibitively expensive for any routine method of water testing or screening.

2b. Assays in Mice

The "orthoptic mouse" model teaches a method in which cells from an established tumor cell line are transplanted into a nude (immunologically compromised) mouse. The recipient mouse is then treated with the chemical agent of interest, and sacrificed, and the effect of treatment on the transplanted tumor is then observed in tissue sections. See Wang et al., Cancer Research 54, 4726–4728 (1994); Hoffman R, J. Cellular Biochem. 56, 1–4 (1994).

Limitations. The chief limitations in methods which involve the orthoptic mouse model involve: (1) access to only juvenile and adult life-stages; (2) high degree of technical skill; (3) high cost; and (4) ethical constraints on working with mice.

3. Prior Art in the Field of Environmental Testing: Embryo Toxicity Assays

Over the years a great variety of short-term toxicity assays, ranging from microbial assays to eukaryotic cell line assays; have been developed for use in toxicological investigations of environmental contaminants. For example, cultured cell lines have been widely used by toxicologists. Their utility is compromised by the problems that cell lines can carry accumulated load of genetic mutations and defects, and that standardization between different laboratory isolates of the same cell line may vary. These are essentially the same problems as described for cell-lines in the context of pharmaceutical testing (above). With cultured fish cell lines (primarily rainbow trout), it is impossible to assay at the three different life-stages, which is a key teaching of the present invention.

Toxicologists have also displayed interest, albeit limited, in the use of intact embryos in toxicity testing. For example, in assays for apoptosis as induced by various physical and chemical environmental factors, there have been only two published reports employing embryos. In these reports, gestational day 10–11 rat conceptuses and preimplantation rabbit embryos have been evaluated for susceptibility to apoptosis in response to peptidyl diazomethanes and radiation, respectively. See Ambroso J L and Harris C. Teratology 50(3):214–228 (1994); Hegele-Hartung, C., et al., Anat. Embryol. (Berlin) 178 (3):229–241 (1988). The lack of widespread use of whole embryos in testing for environmentally-induced apoptosis may testify to the technical difficulties of research using in vitro testing of whole mammalian embryos.

Fish embryos, both marine (herring, mackerel) and freshwater (rainbow trout, zebrafish) have been used in the past by aquatic toxicologists. The biomarkers used in these fish embryo toxicity assays can be summarized according to the following Table (THIS=this invention; n.a.=not applicable; [#]=prior art reference discussed below; none=no prior art reference found).

TABLE I

Summary of Prior Art: Fish Embryo Tests.

| fish embryo life-stage | TESTING ENDPOINT | | | |
|---|---|---|---|---|
| | lethality | teratogenicity | apoptosis | cytogenetic defects |
| embryo: pre MBT | [1, 2] | n.a. | none | THIS; [3, 4, 5] |
| embryo: MBT to mid-gastrula | [1, 2] | n.a. | none | THIS; [3, 4, 5] |
| embryo: mid-late gastrula | [1, 2] | [1] | THIS | THIS; [3, 4, 5] |

TABLE I-continued

Summary of Prior Art: Fish Embryo Tests.

| fish embryo life-stage | TESTING ENDPOINT | | | |
|---|---|---|---|---|
| | lethality | teratogenicity | apoptosis | cytogenetic defects |
| embryo: somitogenesis | [1, 2] | [1] | none | none |
| embryo: organogenesis | [1, 2] | [1] | none | none |

The above table presents a conceptual framework for analysis of prior art for fish embryo bioassays. Papers [1] and [2] are representative of a class of papers which scores very broad and non-specific defects (such as lethality and teratogenicity, or body-pattern defects). For example, [1] refers to a study where ten chemicals were screened against both the RTG-2 (rainbow trout gonad) cell line in a live/dead test and against zebrafish embryos, up to 96 hours of age, for lethality and for teratogenic (body-patterning) defects. See Lange M. et al. Chemosphere 30, 2087–2102 (1995). In reference [2], rainbow trout eggs were injected with halogenated aromatic hydrocarbons and the mortality at hatching was measured. See Walker et al. Aquat. Toxicol. 22: 15–38 (1992). The above Table shows that this class of papers in fact does not overlap with the claims of the present invention.

Prior art which is the most directly relevant to the present invention is represented by a set of three publications, designated [3,4,5] in the above Table. These relate to assays for cytogenetic defects in embryos of teleosts (bony fish). See [3] Longwell A C & Hughes J B, Rapp. P., v. Reun. Cons. Int. Explor. Mer. 179, 275–291 (1980); [4] Liguori V M & Landolt M L in "Short-Term Bioassays in the Analysis of Complex Environmental Mixtures IV (eds M D Waters et al.), Plenum Press, New York (1985); [5] Kocan R M & Landolt M L in "In Situ Evaluations of Biological Hazards on Environmental Pollutants" (eds S S Sandhu et al.), Plenum Press, New York (1990). All of these papers teach a similar method that involves exposing early life-stage embryos to a genotoxic agent, then fixing the embryos with acetic acid or methanol, then making "embryo squashes" which are stained with the nuclear-specific, chemical deposition-based stain aceto-orcein.

It is important to note that there is no prior art on the use of apoptosis as an endpoint for genotoxicity testing using fish embryos. Apoptosis has been used, however, as an endpoint for mammalian whole embryo testing, as described above.

Limitations: The fish embryo assays described in the prior art references of [3, 4, 5] have the following limitations. (1) The assays were developed at a time in history when there was no scientific knowledge about the different phases of activation of cell-cycle checkpoints during embryonic development. Therefore, it was not possible to conceive of applying the assay under different cell-cycle checkpoint regimes, to allow different sensitivity ranges and classes of phenotypes to be examined. (2) No particular care was taken to insure that the treatment was applied at a well-defined developmental stage, or that embryos were synchronous in their development. This clearly is of critical importance, based on the foregoing discussion of "Background Knowledge from the Field of Developmental Biology". (3) Prior art embryo assays using the Rainbow Trout, a cold-water temperate freshwater fish species which is a standard in environmental compliance testing in North America, suffer from a long incubation time required for the normal development of a cold-water fish species. Rainbow Trout eggs hatch in 4 to 7 weeks, while zebrafish (a tropical fresh-water fish species) embryos hatch in 3 days. (4) The embryo squashes described in prior art employed embryos of cold water fishes (mackeral, herring, trout). The embryos of these fishes take many days to reach the end of gastrula stage, hence their mitotic activity is low. Cytogenetic defects related to aberrant passage through mitosis therefore are rare events, and hard to detect for this reason. (5) Either the natural opacity of the embryos, or the method of fixation (methanol/acetic acid), or both, leads to a pronounced lack of transparency. This means that, at best, one cell layer can be examined. However, I have determined that in such a "squash" there can be as many as 5 cell layers, implying that up to 80% of the potential information is lost in an opaque specimen. (6) Staining by a chemical deposition process (e.g. aceto-orcein) produces poor resolution and loss of internal gradations of detail within structures. Only defective anaphase figures can reliably be observed in the prior art examples, whereas in the present invention, many subtle defects in all phases of the cell cycle are immediately apparent.

4. Final Summary of Prior Art

From the above discussion, it is clear that all established vertebrate genotoxicity assay systems suffer from one or more limitations, including: (1) lack of access to different developmental stages (for example, with cultured cell lines), (2) high background level of pre-existing cytogenetic abnormalities (for example, with cultured cell lines), (3) lack of optical transparency (for example, with squashes of embryos fixed in methanol or acetic acid), (4) high degree of technical skill (with mammalian cell-culture, mammalian embryo, and mouse models), (5) high cost (with mammalian cell-culture, mammalian embryo, and mouse models), or (6) ethical constraints (with mammalian embryo and mouse models).

OBJECTS AND ADVANTAGES

It is an object of the present invention to teach a bioassay method for detection of apoptosis and cytogenetic defects, using different embryo life-stages of teleosts (bony fish). Specifically, a method is taught in which teleost embryos are ectopically exposed, at three or more different life-stages, to a suspected genotoxic agent in an aqueous medium. Embryos are then fixed, dechorionated, deyolked, stained for chromosome morphology and cytogenetic defects, and also stained for fragmentation of DNA that is associated with apoptosis. The embryos are then examined, in the form of "flattened whole mounts", by epifluorescence microscopy, at a resolution approaching the Rayleigh limit.

It is a further object of the invention, that the method which is taught should be free of the shortcomings found in examples of prior art. These limitations include: (1) lack of access to different life-stages; (2) slow development and low mitotic index in cold water fish embryos and in cultured cell lines; (3) high background level of pre-existing (spontaneous) cytogenetic abnormalities; (4) lack of optical transparencies; (5) high level of technical skill required; (6) high cost per assay; (7) ethical constraints.

Several objects and advantages of this invention are as follows.

(1) The assay allows genotoxic effects to be scored at three different life stages, which display different sensitivity ranges toward genotoxic agents, and which also display different ranges of possible phenotypes. The assay may be done before MBT (before cell-cycle checkpoints have become operative). It may also be done after MBT (when cell-cycle checkpoints are operative). Finally, it may be done after MGT when the teleost embryo has acquired a capability for apoptosis. This stands in sharp contrast to studies on adult fish or in cultured fish cell lines, which are conducted exclusively in the adult life stage.

(2) The assay appears to be the only one in the literature which specifically tests fish embryos for apoptosis as a phenotypic response to genotoxic agents from environmental samples. We have determined by laboratory tests that certain genotoxic agents which fail to induce cytogenetic defects will induce apoptosis instead, and therefore will be detectable.

(3) The newly-conceived zebrafish embryos are pristine and undamaged, showing only a very low level of spontaneous cytogenetic defects (a typical defect frequency <0.001 up to the 10,000 cell stage). This stands in sharp contrast to the profound genetic damage which typically is carried in cancer cell lines or immortalized cell lines.

(4) Due to the high degree of transparency of certain teleost embryos, and to the method of sample preparation described herein, the assays allow detection of cytogenetic defects and apoptosis in all individual cells of an embryo up to the 10,000 cell stage. This stands in sharp contrast to the prior-art embryo squash methods in which optical transparency is either not present initially, or is lost during fixation or staining.

(5) With this assay, it is possible to avoid confocal microscopy, which is expensive and technically difficult.

(6) The assay is quantitative, as further described by example #7 in the "preferred embodiment" section below.

(7) The invention is rapid, and partially automatable, and cost-effective. A cost-comparison of prior art methods was undertaken by the International Program for the Evaluation of Short-Term Tests for Carcinogenicity. In prior art methods, the cost per assay was reported to range from $US 1,400 to $11,400 (1981 dollars). See deSerres F J & Ashby J (eds) Evaluation of Short-Term Tests for Carcinogens: report of the International Collaborative Program, Elsevier, N.Y. (1981); Lave L B & Omenn G S, Nature 324, 29–34 (1986). In sharp contrast, a cost-estimate of the zebrafish embryo assay as descibed in the present invention is $US 300 per assay (1997 dollars). This represents at least a ten-fold improvement in cost/benefit ratio over existing prior-art methods.

Still further objects and advantages will become apparent from a consideration of the fundamental biology of the zebrafish as a model system. See Eisen, J S Zebrafish Makes a Big Splash, Cell 87, 969–977 (1996); and Development, Volume 123, December 1996, Company of Biologists, Ltd., (a special issue of the journal containing 37 publications describing mutations in genes that affect nearly every aspect of zebrafish development). Some of these objects and advantages are as follows.

(8) Genetic variability can be minimized through use of clutches of sibling embryos obtained by pairwise matings, or of gynogenetic clones which are made artificially diploid by early pressure or heat shock treatment. See Streisinger G., Natl. Cancer Inst. Monogr. 65, 53–58 (1984).

(9) It is possible to use transgenic strains or deletion strains of zebrafish, which may be sensitized to particular types of genotoxic compounds. See Goldsworthy T L et al. Fund. Appl. Toxicol. 22, 8–19 (1994).

(10) This assay may have significance as a predictor of the behavior of whole-animal systems. Short-term acute toxicity tests on fish embryos have been correlated with long-term biological effects, such as pathological conditions or tumors in treated fish that have survived to adulthood within the same experiment. See Liguri and Landolt, Short-Term Bioassays in the Analysis of Complex Environmental Mixtures IV. Plenum Press, New York, 1985; Kocan and Landolt, In Situ Evaluations of Biological Hazards of Environmental Pollutants, Sandhu et al. (Editor), Plenum Press, New York, 1990. Tumorigenesis assays in juvenile or adult fish normally take at least ten weeks depending on the species. See Stanton, M F. J. Natl. Cancer Inst. 34, 117–123 (1965); Khudoley V V. Natl. Cancer Inst. Monogr. 65, 65–70 (1984). In contrast, the present invention could give predictive information on adult zebrafish phenotypes in one to two days.

Still further objects and advantages will become apparent from a consideration of the ensuing description, accompanying drawings, and examples.

PREFERRED EMBODIMENT—DESCRIPTION

Figure 1:
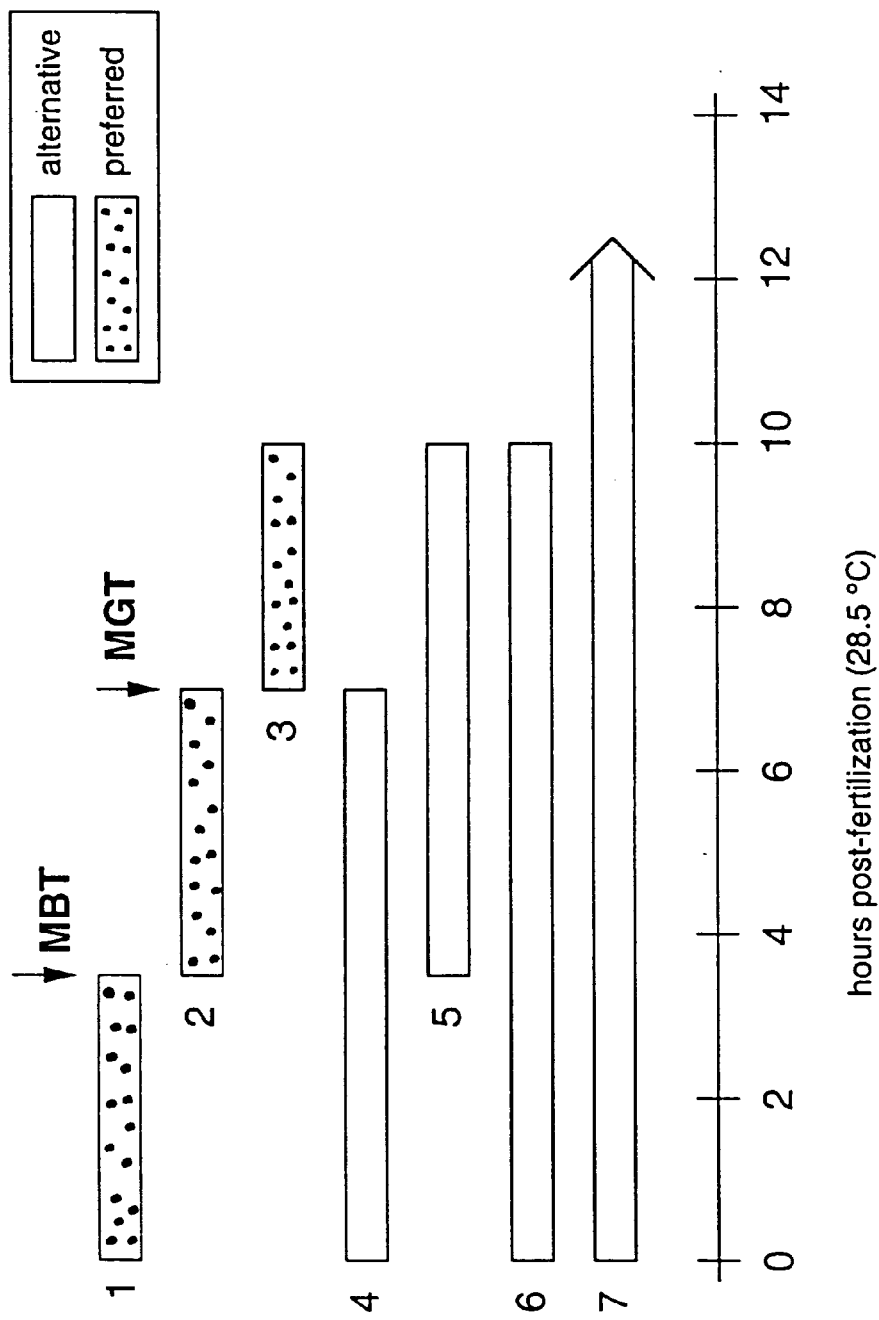
FIG. 1 shows different time-periods for treating a teleost embryo with a test medium, which correspond either to the three developmental life-stages (shaded boxes), or to alternative time-periods (unshaded boxes).
Figure 2:
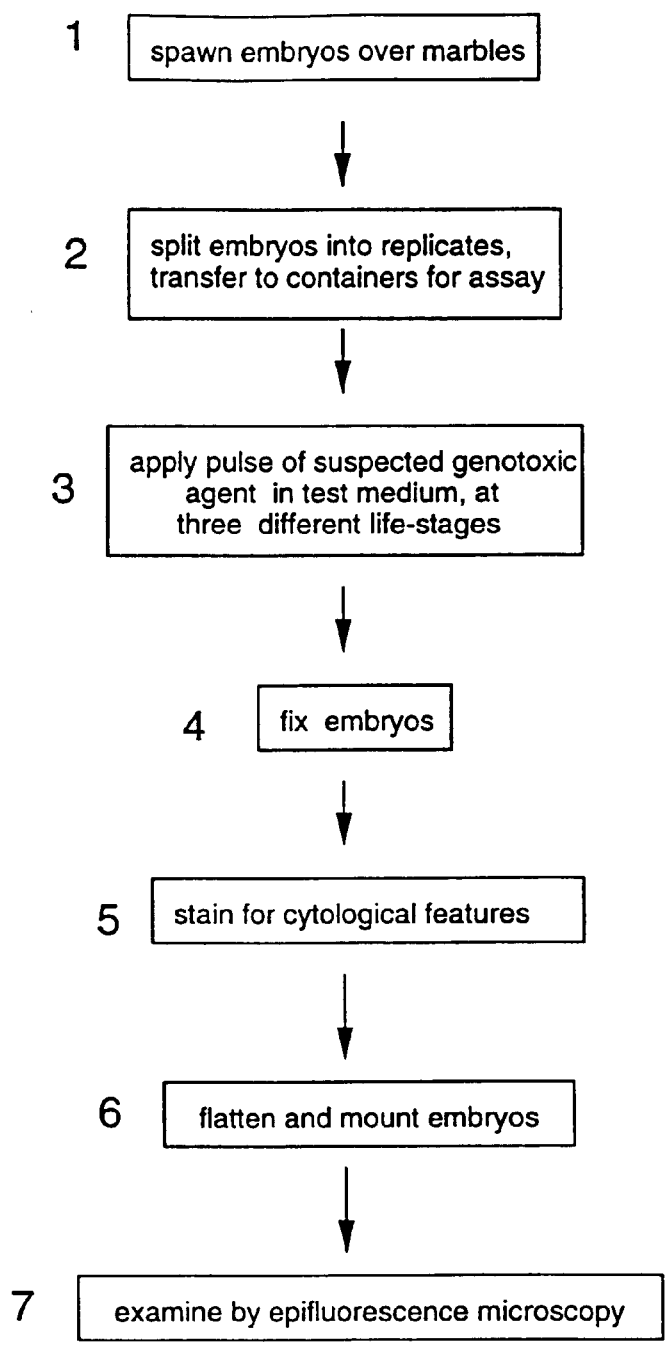
FIG. 2 shows a flow-chart of the method for detecting cytogenetic abnormalities in the "flattened whole-mount" format (preferred embodiment).
Figure 3:
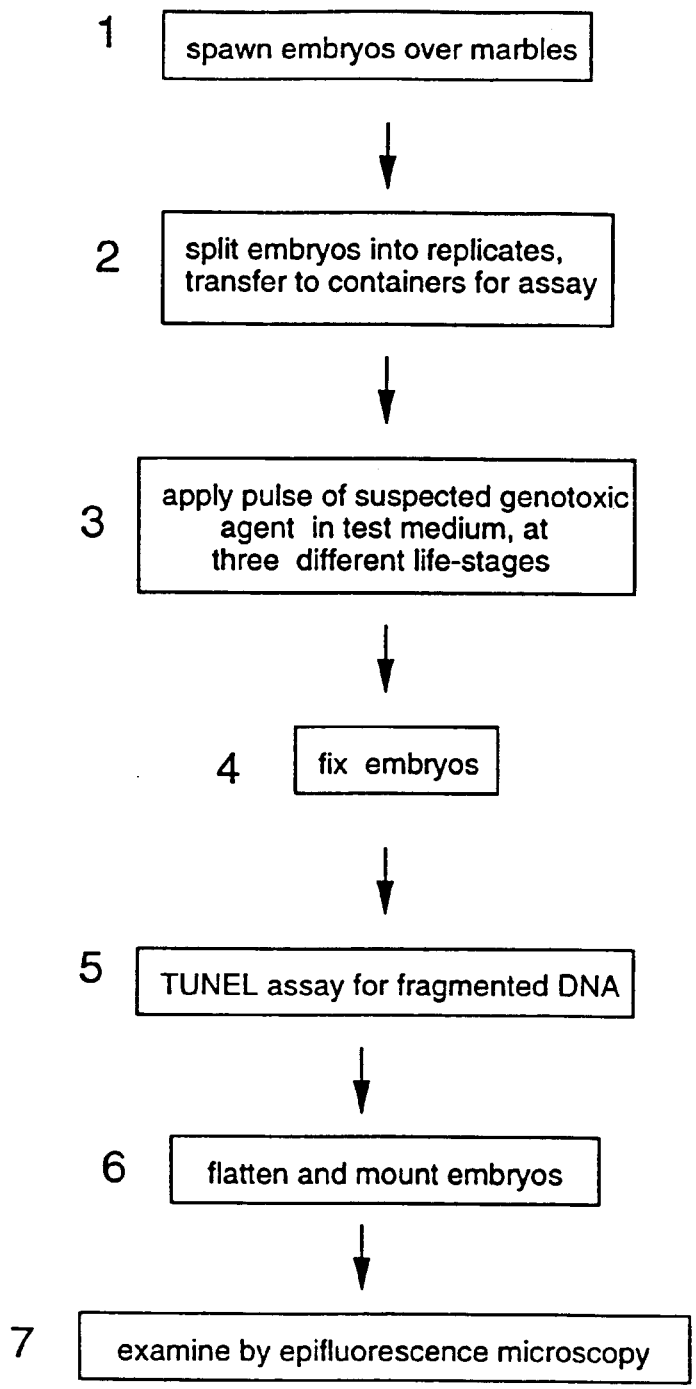
FIG. 3 shows a flow-chart of the method for detecting apoptosis by means of a fluorescent version of the TUNEL assay in the "flattened whole mount" format (preferred embodiment).
Figure 4:
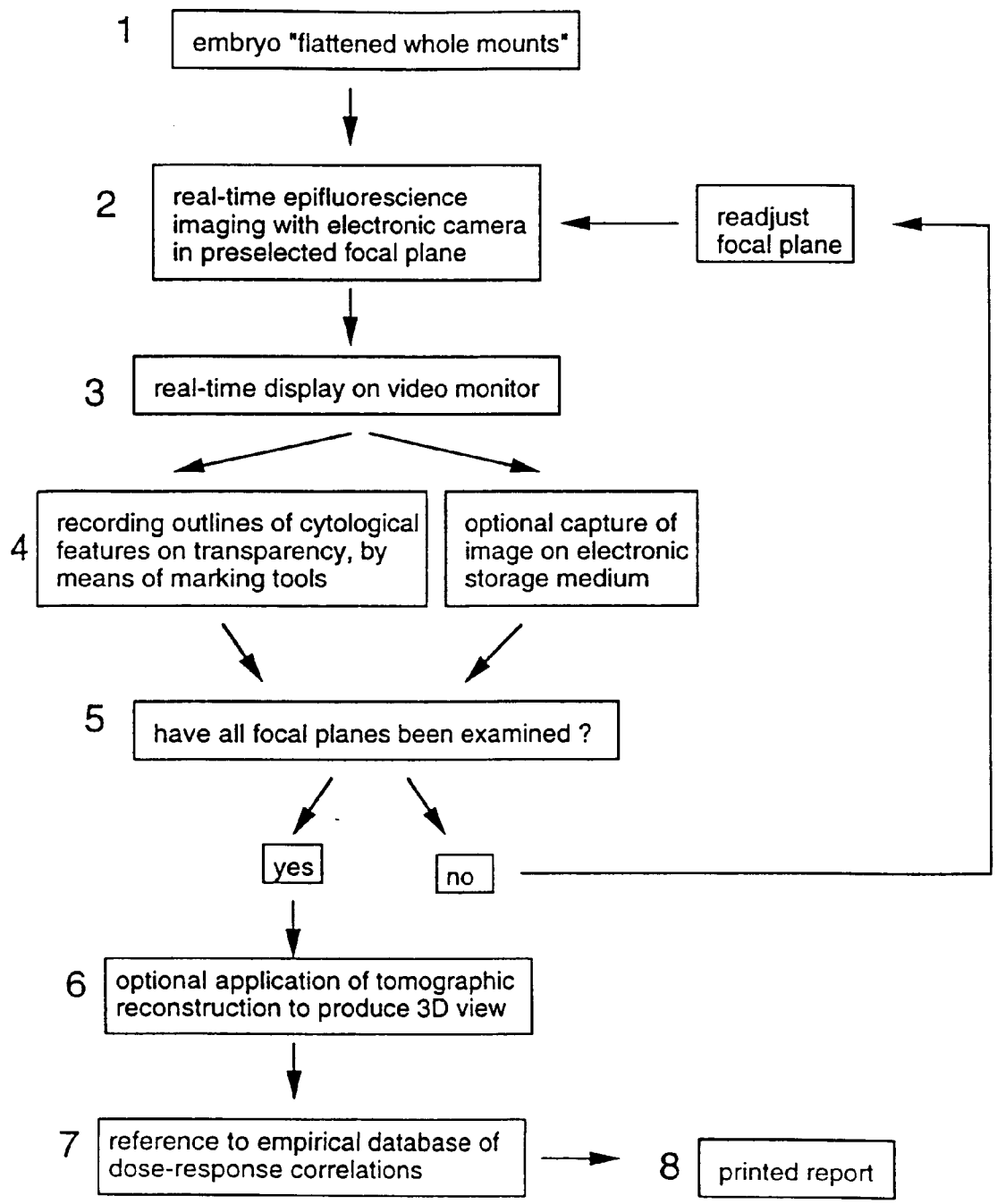
FIG. 4 shows a strategy and flow-chart for generating a quantitative and interpretive report, presenting the results of a teleost embryo genotoxicity test.

A number of technical terms are used in the description of the invention, and in the statement of the claims. These terms will now be defined.

TABLE 2

Table of Definitions.

| | |
|---|---|
| Apoptosis — | a process of programmed cell death, characterized by cell-surface blebbing, degradation of cell nuclei and chromatin, and lack of inflammation of surrounding tissue. |
| Biochemical Test — | an in vitro test which involves a specific enzymatic activity or binding interaction, for example a binding interaction with a specific antibody. |
| Biological Test — | an in vivo test which involves the response of a living organism or embryo. |
| Checkpoint — | a mechanism internal to a cell which monitors a state or process within that cell, such as integrity of genetic material or fidelity of DNA replication; if the monitored state or process falls outside acceptable limits, then a response such as cell-cycle arrest or apoptosis is initiated. |
| Chorion — | a tough proteinaceous membrane around the embryo, which is created at fertilization and from which the embryo hatches. |
| Chromosome — | a macroscopic object consisting of the DNA in a single genetic linkage group, plus all associated structural proteins. Observable in light microscopy during mitosis. |

TABLE 2-continued

Table of Definitions.

| | |
|---|---|
| Chromatin — | a natural complex between DNA and DNA-binding structural proteins such as the histones. |
| Chromogenic — | relating to a chemical or physical process which produces an optically detectable signal. |
| Epiboly — | a process of cell-movement which occurs in an embryo during gastrulation, resulting in the formation and juxtaposition of different cell-layers. |
| Focal Plane — | a positional range, along an optical axis, in which a microscope objective collects rays to produce a sharp image at the image plane. |
| G1 phase — | phase of the cell-cycle which lies between M phase and S phase |
| G2 phase — | phase of the cell-cycle which lies between S phase and M phase. |
| Genotoxic — | producing mutations in the DNA of an organism. |
| Label — | an atomic, molecular, or macromolecular group which can be detected in some fashion, for example by an optical techique. |
| Flattened Whole Mount — | a tissue sample which has been reduced in thickness by applying pressure; in a flattened whole-mount, the three-dimensional relationship between constituent cells typically has been retained. Compare Squash. |
| Mid-Blastula Transition (MBT) — | a developmental milestone, occurring around 10th–12th cleavage division, when the cell-cycle changes from the "embryonic" to the "adult" form. |
| M phase — | phase of the cell-cycle in which the replicated DNA is paritioned to daughter cells. |
| Parthenote — | an embryo for which only the egg or, less commonly, only the sperm has contributed genetic material. |
| Particulate radiation — | radiation containing protons, electrons, neutrons, or other subatomic particles. |
| Phosphor-imager — | a device for obtaining a 2-dimensional spatial representation of a beta-emission source, based on excitation, by the beta radiation, of a 2-dimensional matrix of fluorophores. |
| Rayleigh Limit — | theoretical limit of spatial resolution in light microscopy, equal to $\lambda/2$ (NA) where $\lambda$ = wavelength of light and NA = numerical aperature of microscope objective. |
| S phase — | phase of the cell-cycle in which the DNA is replicated. |
| Squash — | a tissue sample which has been reduced in thickness by applying pressure; in a squash, the three-dimensional relationship between constituent cells typically has been perturbed or lost. Compare Flattened Whole-Mount. |
| Stain — | a solution or suspension containing a label in a carrier phase. |
| Teleost — | relating to bony fish, in which the skeleton is fully ossified. |
| Tomography — | a technique by which a three-dimensional representation of an object is constructed from a series of two-dimensional sections or projections. |
| Yolk — | a complex mixture of macromolecules, loaded into an egg by the mother, by which an embryo receives sustenance before and while it is learning to ingest food. |
| Zygote — | an embryo for which both the egg and sperm have contributed genetic material. |

The present invention provides a method to detect cytogenetic defects and apoptosis, as induced by ectopic application of a test medium, at three different life-stages in embryos of teleosts (bony fish). In the preferred embodiment of the invention, the following items are used.

(1) A standard aquaculture facility is used to produce embryos. For zebrafish, a standard facility is one in which adults of both sexes are housed together in recirculating tanks of deionized water+60 mg/L sea salts, on a 14 hour light/10 hour dark cycle, at 28.5 degrees Celsius. See Westerfield, M. The Zebrafish Book, 3rd Edition. University of Oregon Press, Eugene, Oreg. (1993). For other teleost embryos, appropriate aquaculture system designs can be obtained from the scientific or trade literature. See "Aquaculture Supply Catalog", Florida Aqua Farms, Inc. Dade City, Fla. (1996).

(2) Containers for incubation of embryos with the test media are flat-bottomed, and constructed of an inert material. In the preferred embodiment, 2.0-ml polypropylene flat-bottomed micro-centrifuge tubes are used. The containers are covered to prevent evaporation, and are placed within an incubator maintained at the temperature that is optimum for the teleost species being examined.

(3) The teleost embryos are exposed to serial dilutions of the test medium at each of the three different developmental life-stages. These life-stages are characterized by different states of cell-cycle checkpoint activation, and consequently by different sets or ranges of possible phenotypes which may be induced by treatment with a test medium.

Stage 1—occurs between fertilization and midblastula transition (MBT). The MBT occurs around 10th–12th cleavage division in teleost embryos. For zebrafish, the MBT occurs about 3.5 to 4.5 hours after fertilization, when embryos are incubated at 28.5 degrees Celsius.

Stage 2—occurs between MBT and the period of 70% epiboly. For zebrafish embryos at 28.5 degrees Celsius, the 70% epiboly point occurs around 7 hours post-fertilization.

Stage 3—occurs between 70% epiboly and 100% epiboly (the end of gastrulation). For zebrafish embryos maintained at 28.5 degrees Celsius, the end of gastrulation occurs around 10 hours post-fertilization.

(4) Chemical fixative. Embryos are fixed in a fixative that maintains optical transparency. As an example but not a limitation, 4% formaldehyde in PBS or PEM buffer is acceptable for zebrafish embryos. PBS (phosphate-buffered saline)=0.8% NaCl, 0.02% KCl, 20 mM phosphate (pH 7.3). PEM (Patel et al., Cell 58, 955–968. 1989)=0.1 M PIPES (pH 6.95), 2.0 mM EGTA, 1.0 mM $MgSO_4$.

(5) Dechorionation. The preferred tools for manual dechorionation are a pair of Dumont #55 Biologie forceps, a zoom stereomicroscope, and a fibre optic illuminator. One forceps is held and manipulated with each hand, under 40× magnification provided by the stereomicroscope, using oblique side illumination from the fibre optic lamp.

(6) Deyolking. The preferred tools for manual deyolking a pair of Dumont #55 Biologie forceps, a zoom stereomicroscope, and a fibre optic illuminator. One forceps is held and manipulated with each hand, under 40× magnification provided by the stereomicroscope, using oblique side illumination from the fibre optic lamp.

(7a) Staining for nuclear or chromosome morphology. A DNA binding dye is used to detect nuclei and chromosomes. By means of example and not limitation, a high signal/background ratio is obtained with Hoechst 33258.

(7b). Staining for fragmented DNA, especially in the period between midgastrula and late gastrula. This is achieved with a modified version of the TUNEL assay, in which a terminal deoxynucleotidyl transferase enzyme is used to incorporate a fluorescent label into the 3'—OH termini of broken DNA strands in an embryo. In the preferred embodiment the TUNEL assay is performed on a flattened whole-mount.

(8) Epifluorescence microscopy. To achieve acceptable or optimum resolution, plan-fluorite or plan-apochromatic objectives of following numerical aperatures should be used: 10×, NA≧0.5; 40×, NA≧0.75; 100×, NA≧1.30 (oil immersion).

The Rayleigh criterion sets the limit on the maximum spatial resolution (R) which can be achieved in the specimen plane:

$$R=\lambda/(2*NA) \quad (3)$$

See Slayter and Slayter, Light and Electron Microscopy. Cambridge University Press (1992). With the above specifications on the microscope objectives, the nuclei and chromosomes within a flattened whole-mount of the zebrafish embryo can be imaged at a spatial resolution which approaches the Rayleigh limit, using conventional (non-confocal) epifluorescence microscopy.

If double-labelling is to be used, then the microscope must be equipped with the appropriate dichroic filters. By way of example but not limitation, a useful choice of filters for resolving red fluorescence from a rhodamine-conjugated or Texas Red-conjugated antibody stain, and a Hoechst 33258 nuclear counterstain, is: Zeiss #15 filter set for red channel (excitation wavelength 540–550 nm, emission wavelength>590 nm), and Chroma #31000 filter set for blue channel (excitation wavelength 320–390 nm, emission wavelength 433–494 nm).

(9.) Image Capture. High-resolution images are captured either on photographic film, or digitally with a CCD camera and frame-grabber. As an example but not a limitation, good results will be obtained using black-and-white film with a stated resolution of at least 70 line-pairs per millimeter. Possible choices for film include Kodak T-Max 100, Kodak T-Max 400, Ilford Delta 100 or Ilford Delta 400. Film should be processed in matched developer under the "highest resolution" protocol according to the manufacturer's instructions.

PREFERRED EMBODIMENT—OPERATION

In the preferred embodiment, the examiner places the teleost embryo into a test medium, prepares the embryo for subsequent cytological examination by a procedure which fixes the embryo, removes the chorion and yolk, adds a cytological stain, flattens the embryo, and then obtains high resolution spatial information on a variety of cytological features within cells of the embryo.

(1) Embryos are collected from mature adult fish spawned under laboratory conditions according to well established husbandry procedures. For zebrafish, embryos are collected over marbles from aquaria where adults are maintained in groups of 5 males to 10 females on a light/dark photocycle. The adult fish are fed twice a day with a dry flake fish food (for example, TetraMin) and at least once a week with living larvae of brine shrimp, Artemia salina. See Westerfield, M. The Zebrafish Book, 3rd Edition. University of Oregon Press, Eugene, Oreg. (1993). Dead or defective embryos are discarded.

(2) Sets of embryos (3 sets per treatment, with typically 3–5 replicate embryos per set) are transferred to 2.0-ml polypropylene flat-bottomed tubes, with a fire-polished glass eye-dropper or pipette.

(3) A test medium is applied, at a series of dilutions, to sets of replicate embryos, at three different life stages:

(i) Before mid-blastula transition (MBT, 10th cell division) when cell-cycle checkpoints are inoperative. If the test medium is inert, then the cells of the embryo will proceed through the phases of the cell cycle and will appear normal as defined and described in a standard cell biology textbook. As an example but not a limitation, if the embryo is exposed to a test medium which is not inert, but rather which blocks an elementary step in the cell cycle, then because of a lack of cell-cycle checkpoints, individual cells of the embryo will attempt to proceed beyond the block. Gross defects in nuclear and chromososmal structure will result, which are easily observed under the microscope and which are often lethal.

(ii) After MBT but before mid-gastrula transition, when cell-cycle checkpoints are operative but before the capability for apoptosis has appeared. If the test medium is inert, then normal progression through the cell cycle will occur, as before. As an example but not a limitation, if the embryo is exposed to a chemical agent which interferes with the operation or progression of cell-cycle, the cells of the embryo will arrest and this arrest will be observable at the level of the whole embryo, and also at the level of individual nuclei.

(iii) After mid-gastrula transition, when the embryo is able to undergo apoptosis. If the test medium is inert, the cells of the embryo will appear normal as before. As an example but not a limitation, if the test medium contains a substance which contains a genotoxic agent, a proportion of the cells of the embryo will enter into a state of apoptosis, in direct proportion to the toxicity of the chemical substance.

At each of the three life stages, the embryos are exposed to a series of concentrations of each test solution for a predefined length of time, usually 1–2 hours.

(4) After treatment, the embryos are fixed with a chemical agent which quickly kills them, prevents further changes, and also renders them permeable to subsequent treatments. A 4% formaldehyde solution in PBT works well for zebrafish embryos at the three life stages of interest.

(5) Dechorionation Procedure. Dechorionation is done under 40× stereoscopic magnification. One forceps is held and manipulated with each hand. The chorion is grasped with two Dumont #55 forceps, and gently a tear is made. The embryo then falls through the tear by force of gravity.

(6) Deyolking Procedure. For deyolking, the embryo is transferred to an agarose-coated petri dish in embryo medium, using a drawn and fire-polished Pasteur pipette. The yolk is then ruptured with a Dumount #55 forceps and a minutien pin. Fragments of yolk are carefully "scooped out" from the interior of the embryo, and then washed or swept away.

(7a) Staining for nuclear or chromosome morphology with a DNA binding dye. In a preferred embodiment, a DNA binding dye is used to detect nuclei and chromosomes. DAPI, Hoechst, and ethidium bromide were also tested for utility in staining for nuclear morphology. In this case, DNA and not histone is being detected. DAPI staining was conducted at 5 μg/ml dye concentration for 15 min. Hoechst staining was conducted at 0.5–10 μg/ml dye concentration in PEM for 30 min-24 hours in the dark at 4° C. Embryos were then destained for 10 min-144 hours in several changes of PBS at 4° C. These dyes produce a large amount of autofluoresence if they partition into the yolk. They also produce some autofluoresence in the cytoplasm. The embryos therefore must be deyolked, in order to image nuclei or chromosomes using these dyes. A moderate or high degree of fixation will toughen the cell layer sufficiently that the embryo can be deyolked before beginning the staining. The background fluoresence in cells of early embryos (<64 cell stage) is significantly higher with DAPI or Hoechst than for staining with anti(HI)+rhodamine-conjugated anti(IgG). Thus DAPI or Hoechst dyes are best suited for staining embryos that have developed beyond the 64-cell stage.

(7b). Staining for fragmentation of DNA associated with genotoxic damage. In the preferred embodiment, the TUNEL assay is used to detect 3'OH termini of nicked or broken DNA strands. These nicks or breaks may be generated directly by a genotoxic agent or indirectly through the triggering of apoptosis (a programmed cell death response).

(8) Flattening Procedure. The deyolked and stained embryo, consisting of a sheet or "cap" of cells, is then transferred with the fire-polished pipette to a clean glass microscope slide. A coverslip of known thickness is then gently placed upon the drop of buffer which contains the cap or sheet of cells. The weight of the coverslip is sufficient to flatten the embryo. If the procedure is done with sufficient care, then different cell-layers within the embryo will be preserved in the flattened whole-mount. For example, gastrula-stage zebrafish embryos have three different cell-layers (the enveloping epithelial layer, the deep layer, and the yolk syncytial layer). These layers occupy different focal planes along the optical axis (z-axis) in the flattened whole-mount, and therefore can be examined for differential responses to a genotoxic agent (see Example 6). If the edges of the coverslip are then sealed with nail polish, the flattened whole-mount will retain morphological integrity of its nuclei for more than one week when stored at 4° C. If the coverslip edges are not sealed, then evaporation and sample degradation will occur rapidly.

(9) Epifluorescence microscopy and photography. In the preferred embodiment, microscopy is performed with a conventional (non-confocal) epifluorescence microscope. It is necessary to mount the microscope on a pneumatic air-table to damp out vibration. If film exposures are to be made, then it is necessary to limit photographic exposures to <1 minute, and to use a vibration-free magnetic shutter camera to obtain blur-free photographs. Images are recorded with high-resolution black/white film. By way of example but not limitation, a high-quality image can be obtained using Kodak Tmax 100 or 400 film, or Ilford Delta 100 or 400 film. Film negatives are developed with Tmax or Ilfosol S developer and selected film negatives are printed on Ilford Multigrade IV medium-contrast glossy paper.

EXAMPLES

Certain embodiments of the invention are described in the following non-limiting examples.

Example 1

Empirical Determination of the Times of Three Life Stages of Early Development of Embryos of an Arbitrary Teleost Species To apply the method of the invention to embryos of an arbitrary teleost species, one first must experimentally determine the time-course of the early life stages in the embryonic development of that species. The three life stages will be associated with different sets of possible phenotypes. It will be appreciated that the developmental time-course of embryos of a particular teleost species will be unique to that species, and therefore must be empirically determined. Embryos of a teleost of interest are obtained by spontaneous mating of adults, or by in vitro fertilization, according to established methods. For example, the routine production of zebrafish embryos is described in Westerfield, M. (ed) The Zebrafish Book, 3rd edn. University of Oregon Press, Eugene, Oreg. (1993). At each of a series of times after fertilization, embryos are exposed for 1 hour to either buffer, or to one or more agents which interfere with operation of the DNA replication apparatus, and thus prevent completion of S phase. (For zebrafish, every hour, on the hour, up to 10 hours after fertilization is appropriate. The end of gastrulation is reached at 10 hours after fertilization.) Suitable agents for blocking the DNA replication apparatus include 25 µg/ml aphidicolin (an inhibitor of DNA polymerase alpha) and 60 µM camptothecin (an inhibitor of topoisomerase I).

Example 2

Detection of Cytogenetic Defects with Alternative DNA-Binding Dye

Three DNA-binding dyes DAPI, Hoechst, and ethidium bromide were tested for utility in staining for nuclear morphology. In the currently optimized protocol, Hoechst dye was found to give the lowest background, and so is chosen for the preferred embodiment. However other DNA dyes may be used instead. In the current optimized protocol, embryos are fixed in 4% formaldehyde, dechorionated, deyolked, stained with Hoechst 33258 dye, and then destained for 10–30 min in several changes of PBS at 4° C.

Example 3

Detection of Cytogenetic Defects with Anti (H1) antibody

Nuclei and chromosomes can be detected by indirect immunofluorescence using an antibody against an integral chromosomal protein. Embryos are fixed with 4% formaldehyde, dechorionated, deyolked, and then subjected to a sequence of staining and destaining steps which result in immuno-histochemical labelling of a chromatin protein. They are then flattened and examined microscopically.

Example 4

Detection of Aberrant Interphase Nuclei

This example addresses the limitations of prior-art in which cytogenetic defects are detected in "squashes" of embryos lower vertebrates. The prior-art squashes were not transparent, and so intact cell-nuclei were not easily observed. Furthermore, chemical deposition -based detection methods caused the internal detail within nuclei to be obscured.

Zebrafish embryos are treated, beginning at the 128–256 cell stage, and continuing for 1.5 hours, with 5 µg/ml ionomycin (a Ca++ ionophore). The embryos are fixed, dechorionated, deyolked, and stained with the DNA-binding dye Hoechst 33258. Embryos are then prepared as 'flattened whole mounts' and examined under epifluorescence microscopy at 1,000× magnification. Abnormally large nuclei with fine internal strands of condensed chromatin are observed. This example illustrates that the assay can detect significant internal detail within defective interphase nuclei, which is not possible with prior-art methods.

Example 5

Detection of Apoptotic Nuclei with Fluorescent TUNEL Assay

DNA fragmentation is detected with the terminal transferase assay (TUNEL; Thiry, 1992; Gavrieli et al 1992). The protocols which are described in the above two papers relate to the staining of histological thin sections. The inventor has modified the published protocols to allow detection by epifluoresence microscopy on flattened teleost embryo whole-mounts. Embryos are fixed for 3 hr in 4% formaldehyde in PEM, washed in PBS and dechorionated. Dechorionated embryos are transferred to wells of a glass depression slide for the following operations. They are washed 2× in 100 µl PBT on a rotary shaker for 15 min at room temperature. Next, they are incubated 60 min in fresh PBT+5% normal goat serum on the rotary shaker, and then rinsed twice with PBT.

The embryos are then incubated for 30 min at room temperature on the rotary shaker in 50 µl of ApopTag Equilibration Buffer (Oncor, Gaithersburg, Md.). This is replaced with 50 µl of a 2:1 mixture of Apoptag Reaction Buffer and terminal transferase enzyme solution (Oncor). The embryos are incubated for 2.5 hr at 37° C. Next, 50 µl of a 1:34 mixture of Stop/wash buffer:water, preheated to 37° C., is added to the embryos, and incubation is done for 60 min at 37° C. with gentle agitation every 10 min. Embryos are washed twice with fresh PBT for 15 min at room temperature. This is replaced with PBT+5% normal goat serum, and incubation is done either for 60 min at room temperature on a rotary shaker, or for 16 hours at 4° C. without shaking. The solution is replaced with fresh PBT containing a 1:100 to 1:400 dilution of Texas Red-conjugated anti-(digoxygenin) (Jackson ImmunoResearch). The embryos are incubated for 2 hr at room temperature in the dark. Embryos are washed twice with PBT, deyolked, counterstained in 1 µg/ml Hoechst 33258 for 25 min, and destained in PBT for 60 min at room temperature.

The resultant animal cell caps are prepared as flattened whole-mounts and visualized by epifluorescence microscopy. Red and blue fluorescence emissions are separated well with the following dichoric filters: blue=Chroma #31000 (excitation wavelength=320–390 nm, emission wavelength=433–494 nm); red=Zeiss #15 (excitation wavelength=540–550, emission wavelength>590 nm).

Example 6

Observation of Different Biological Responses in Different Cell Layers of a Flattened Whole-Mount A gastrula-stage zebrafish embryo has three different cell layers (the superficial epithelial layer, the "deep" layer, and the yolk syncytial layer). If the procedure for making the flattened whole-mount is performed properly, then these three cell-layers will occupy different focal planes along the optical axis (z-axis) in the flattened whole-mount. Accordingly, they may be examined for differential responses to a suspected genotoxic agent. Zebrafish embryos were exposed at 6 hours post-fertilization to 0.5 µg/ml nocodazole. At a series of successive times, flattened-whole mounts were prepared. All cells in the superficial epithelial layer were observed to become apoptotic. They entered apoptosis from the G1, S, or G2 phase of the cell-cycle as indicated by the fact that the nuclei had nuclear envelopes. In contrast, the cells in the "deep" layer first entered a prometaphase-arrest state. If the incubation in nocodazole was prolonged, then after several hours they entered apoptosis, but from the arrested metaphase state (without intact nuclear envelope). In contrast to the above two behaviors, the yolk syncytial layer never undergoes apoptosis. Thus, a properly prepared flattened whole mount allows the observation of three different biological responses in the three different cell-layers of the embryo.

Example 7

Collection of Quantitative Data

Zebrafish embryos were treated, beginning at mid-late blastula stage, and continuing for 2 hours, with either 25 µl/ml aphidicolin (a blocker of DNA polymerase alpha) or 60 µM etoposide (a topoisomerase II blocker). The embryos were then fixed, dechorionated, deyolked, and stained with the DNA-binding dye Hoechst 33258. Embryos were then prepared as "flattened whole mounts" and examined under epifluorescence microscopy at 1,000× magnification. By way of example and not limitation, the following hardware and software components and configurations were used. Images (435×350 pixels each) were collected in real time using an 8-bit CCD camera (Cohu Inc, San Diego, Calif.) and a standard frame-grabber board (Maatrox, Quebec) which was mounted in an Intel 486 computer. Images were displayed in real time on an 8-bit greyscale monitor using the "Snapshot" software package (BioScan, Edmonds, Wash.). A Mylar transparency was affixed to the monitor screen, and nuclei were traced with a fine-tipped permanent marker for later statistical analysis. Ambiguities were resolved in real time by adjusting the microscope's plane of focus until a clear image could be obtained.

The cytological features of a zebrafish embryo that can be quantified by the above flattened whole mount method include but are not limited to normal, G1, S, G2, prophase, metaphase, anaphase, telophase figures, and the following abnormal structures: S phase nuclei containing depressions or clefts, aberrantly large G2 nuclei, aberrantly large G2 nuclei with partially condensed chromatin, micronuclei, prophase figures with detached chromososmes, bridged anaphase figures, broken chromosomes, micronuclei, tripolar spindles, multimers of nuclei, stretched or deformed nuclei, fragmented nuclei, and nuclei in early, mid and late stages of apoptosis. This contrasts very dramatically with the few cytogenetic features—bridged anaphase figures and the occasional broken chromosome—that have been identified in the teleost embryo squash techniques in prior art references (see Table I).

Example 8

Positive Detection of Genotoxic Agent in Apoptosis Test, Even when it is not Detected in Cytogenetic Defect Test Camptothecin at 60 µM when applied during the third life stage, induces cytogenetic defects in only a small fraction of cells in a zebrafish embryo. However, it induces apoptosis in virtually 100% of cells in a zebrafish embryo at this life stage. Thus, a genotoxic agent which would be missed by a cytogenetic assay may be detected by the apoptosis assay.

Example 9

Test of Water-insoluble Compounds Using a DMSO Carrier

Many known or potential genotoxic compounds, for example benzo(a)pyrene, have a high aromatic character, and therefore a limited solubility in water. The aqueous solubility of such compounds can often be greatly increased by adding DMSO (dimethyl sulfoxide) to the water, to a final concentration of 0.5–1%. Additionally, the DMSO also facilitates passage of hydrophobic compounds across the plasma membrane. We have exposed zebrafish embryos to 0.5–1% DMSO at various life-stages (before mid-blastula stage, between mid-blastula and mid-gastrula stages, and mid-late gastrula stage). The DMSO did not induce cytogenetic defects or apoptosis above the levels observed in untreated controls. Therefore, DMSO is suitable as a carrier for hydrophobic compounds with low inherent water-solubility.

Example 10

Rapid Screen of Three Known Cancer Chemotherapeutic Agents

A set of experiments was conducted in which three widely-used cancer chemotherapeutic agents were screened with the zebrafish embryo assay. The agents were camptothecin (topoisomerase I inhibitor, tested at 60 µm), etoposide (topoisomerase II inhibitor, tested at 20–60 µM), and taxol (microtubule stabilizer, tested at 50 µM). Embryos were exposed either before MBT, shortly after MBT, or in gastrulation (~60% epiboly) and were then fixed and processed for imaging. Each agent was found to induce both large-scale chromosomal defects and also apoptosis. Therefore each agent would have been flagged as a potentially valuable cancer chemotherapeutic agent by the zebrafish embryo assay.

OTHER EMBODIMENTS

By way of example and not by limitation, other embodiments of the various steps are possible. Some of these are now described.

(1) Alternative Fish Species

There are possibly many other fish species in addition to *Danio rerio* that are suitable test species. The only requirement is that the embryos are optically transparent or there is a clearing agent available which renders the embryos transparent.

(2) Alternative Treatment Windows

A test medium may be applied in a pulse-treatment, over a window in time which does not exactly coincide with any of the three life-stages of the embryos, as descibed in the preferred embodiment and FIG. 1 (shaded boxes). Many time-windows for treatment are possible, which overlap the three life-stages in different ways. Some of these are described in FIG. 1 (open boxes).

(3) Alternative holder for sets of embryos

Sets of embryos for testing may be placed in individual wells of a conventional tissue-culture plate. By way of example but not limitation, a radiation-sterilized 24-well polystryene plate may be used, e.g. a "Nunclon MultiDish" (product # 143982, Nalge Nunc International, Naperville, Ill.). If a polystyrene plate is used, then it must first be coated with a layer of 1% agarose. Uncoated polystyrene will damage the embryos.

(4) Alternative DNA Stains (to reveal cytological features)

In the preferred embodiment, chromosome staining is achieved with Hoechst 33258 which provides a high signal/background ratio. Alternative DNA-specific dyes which may be used successfully include but are not limited to (1) DAPI (4,6-diamidino-2,3-phenyl-indole dihydrochloride) and (2) ethidium bromide. Many other DNA-specific dyes are described in the literature. See Haughland R P. Handbook of Fluorescent Probes and Research Chemicals, 5th ed. Molecular Probes, Inc. Eugene, Oreg. (1992).

(5) Alternative Stain for Cytogenetic Features

Staining for nuclear or chromosome morphology may be achieved with an antibody against an integral chromosomal protein. As an example but not a limitation, primary detection of nuclei and chromosomes is achieved using a mouse monoclonal antibody against the chromosomal protein histone H1 (product # MAB1276, Chemicon, Temecula, Calif.). Secondary detection is achieved with goat anti (mouse IgG) which is conjugated to rhodamine or Texas red.

In an experiment, whole-mount staining with anti (H1) was performed using a standard series of buffers and staining steps. See Patel et al. Cell 58, 955–968(1988). In the primary detection step, mouse monoclonal antibody (product # MAB 1276, Chemicon, Temecula, Calif.) at a concentration of 0.45 mg/ml for 20 hours at 4° C. was used. The secondary detection step was achieved with a goat anti(mouse IgG) conjugated to rhodamine.

(6) Treatment with enhancing agent

If a flattened whole-mount is to be examined for a prolonged period of time under epifluorescence microscopy, it should be protected against the tendency to photobleach. A free-radical scavenger (for example, SlowFade reagent, Molecular Probes, Eugene, Oreg.) is added into the final wash solution, which remains present after the flattened whole-mount is sealed under the coverslip.

(7) Alternative dye sets for fluorescent TUNEL assay

The TUNEL assay for apoptotic nuclei, with nuclear counterstaining, may be achieved through use of many different dyes. The only requirements are: (1) that the dyes used for the TUNEL assay and the nuclear counterstain are spectrally well-separated in their fluorescence emission peaks, typically by several hundred nanometers; (2) that the dyes do not produce a high background by non-specific binding to cytoplasmic, membrane, or extracellular material in the flattened whole-mounts.

By way of example but not limitation, the following dye combinations can be used:

Texas red for TUNEL detection, Hoechst 33258 for nuclear counterstain.

Rhodamine for TUNEL detection, Hoechst 33258 for nuclear counterstain.

Texas red for TUNEL detection, DAPI for nuclear counterstain.

Rhodamine for TUNEL detection, DAPI for nuclear counterstain.

(8) Alternative Means for Collecting Quantitative Data

Film negatives may be digitized through use of various devices. By example but not limitation, the digitization may be achieved using a Nikon LS-1000 film scanner (3,000 dpi resolution), or the Kodak "Photo CD" process.

SUMMARY, RAMIFICATIONS, and SCOPE

It can be seen that the method taught here provides a means to rapidly detect various cytogenetic defects and also the fragmentation of DNA (apoptosis), in a developing fish embryo following exposure to a test medium containing one or more genotoxic agents. The invention has the following unique properties. (1) Three different developmental life-stages may be tested, which allows for three different sets of possible phenotypes. (2) The newly-conceived fish embryos are pristine, showing only a very low level of spontaneous cytogenetic defects, in sharp contrast to cultured cell lines. (3) The preferred embodiment uses tropical fish embryos (for example zebrafish). These have high mitotic activity, hence cytological defects associated with the passage through mitosis are easily observed. (4) Due to the high degree of transparency of certain teleost embryos, which is retained by the method of sample preparation described in the present invention, the assays allows single-cell resolution up to the 10,000 cell stage. (5) The assay is quantitative. (6) The invention is inexpensive, and automation of many component steps is possible. (7) Ethical constraints are minimized because the embryos are teleost (not mammalian), and because only very early life stages are being examined (before the nervous system has been created).

Various other embodiments and ramifications are possible within the scope of the present invention. For example, great flexibility in conducting assays will be evident, from the following considerations. (1) Embryos of a variety of teleosts can be used. (2) The treatment time-window does not need to overlap exactly with one of the life-stages defined in FIG. 1. (3) Embryos can be treated and fixed at one time, and then stained, destained, and analyzed at a different, later time, thus allowing work to be done in modules. (4) A variety of different stains or labels may be used to detect cytogenetic features or apoptosis. (5) The data may be observed without recording, or may be recorded on a storage medium such as film or a computer disk.

Some of the ramifications of the invention are apparent, by considering the multitude of uses to which it may be put. As non-limiting examples, the invention could be used in the following ways: (1) as a dosimeter for exposure to electromagnetic radiation or particulate radiation; (2) to test for airborne genotoxic contaminants by extracting or concentrating such contaminants into an aqueous phase; (3) to test for contamination of groundwater or soils; (4) to assess the toxicity of food additives; (5) to assess the toxicity of pharmaceuticals; (6) to assess the toxicity of additives to soaps, cremes, or cosmetics which are meant to contact the human skin; (7) to assess the toxicity of paints or finishes, which are applied to surfaces that are meant to contact the human skin; (8) to monitor the toxicity of industrial effluents from industries including but not limited to the petroleum and petrochemical industries, the mining, milling and smelting industries, the pulp and paper industries, the textile industry, the organic and inorganic chemical industries, the food-processing industry, and other secondary manufacturing industries; (9) to evaluate the efficacy of processes for detoxification or remediation of wastewater or sewage; (10) to evaluate the efficacy of processes for detoxification or remediation of hazardous industrial wastes; (11) to aid in formal assessments of the natural environment, for example where an evaluation of a watershed's surface and ground waters is needed; (12) in environmental compliance testing of drinking water, groundwater, surface water; (13) to assess the safety of materials or substances in the occupational workplace; and (14) in environmental audits for real-estate transactions.

Although the description above contains many specificities, these should not be construed as limiting the scope of the invention but as merely providing illustrations of some of the presently preferred embodiments of this invention. The scope of the invention should be determined by the appended claims and their legal equivalents, rather than by the examples given.

I claim:

1. A biological method for assay of a test medium, said test medium containing at least one potentially genotoxic agent, and said test medium selected from the group consisting of aqueous chemical solutions, aqueous chemical mixtures, aqueous chemical suspensions, aqueous solutions under the influence of electromagnetic radiation, and aqueous solutions under the influence of particulate radiation, said method comprising at least the following steps:

(a) separately contacting living teleost embryos at the following three different developmental life-stages with said test medium:
  (i) before mid-blastula transition;
  (ii) between midblastula transition and mid-gastrula stage;
  (iii) between midgastrula stage and the end of gastrulation,
(b) exposing said embryos to said test medium for a predetermined length of time,
(c) exposing said embryos to a chemical fixative,
(d) preparing said embryos for subsequent examination, whereby three- dimensional cytological information is preserved at the Rayleigh limit of resolution, by a procedure which consists of the following steps:
  (i) removing the chorions of said embryos,
  (ii) removing the yolks of said embryos,
  (iii) contacting said embryos with a series of staining agents and destaining solutions, whereby at least one label from said staining agents become attached to multiple cytological features, said cytological features selected from the group consisting of DNA, nuclei, chromosomes, chromatin-bound proteins, and chromosome-bound proteins, and
(e) examining said embryos for the residual presence of said label by an optical technique, whereby defects in cytological structures are detected and their frequencies quantified, whereby the presence and efficacy of said potentially genotoxic agent in said test medium is indicated.

2. A method as in claim 1 wherein the order of steps (d)(ii) and (d) (iii) are inverted.

3. A method as in claim 1 wherein said embryos, after staining and destaining, are placed between two surfaces which are then sealed with an airtight seal to prevent drying of said embryos.

4. A method as in claim 1 wherein said embryos are obtained by combining eggs and sperm from female and male adults selected from the group consisting of wild-type members of any marine or freshwater teleost species, natural mutant members of any marine or freshwater teleost species, selectively bred mutant members of any marine or freshwater teleost species, and genetically-engineered mutant members of any marine or freshwater teleost species.

5. A method as in claim 1 wherein said embryos are obtained by combining eggs and sperm from female and male adults selected from the group consisting of wild-type members of the genus Danio, natural mutant members of the genus Danio, selectively bred mutant members of the genus Danio, and genetically-engineered mutant members of the genus Danio.

6. A method as in claim 1 wherein said embryos are parthenotes obtained by parthenogenetic activation of eggs from female adults selected from the group consisting of wild-type members of the genus Danio, natural mutant members of the genus Danio, selectively bred mutant members of the genus Danio, and genetically-engineered mutant members of the genus Danio.

7. A method as in claim 1 wherein said fixative is formaldehyde.

8. A method as in claim 1 wherein said staining agents are selected from the group consisting of fluorescent DNA stains, gold-conjugated DNA stains, chromophoric DNA stains, chromogenic DNA stains, and radioactive DNA stains.

9. A method as in claim 1 wherein said staining agents are selected from the group consisting of fluorescent chromosomal-protein stains, gold-conjugated chromosomal-protein stains, chromophoric chromosomal-protein stains, chromogenic chromosomal-protein stains, and radioactive chromosomal-protein stains.

10. A method as in claim 3 wherein said surfaces are rigid, flat, and transparent.

11. A method as in claim 1 wherein said examination is performed with an instrument selected from the group consisting of brightfield microscopes, darkfield microscopes, phase-contrast microscopes, differential interference contrast microscopes, confocal epifluorescence microscopes, non-confocal epifluorescence microscopes, phosphorimagers, and two-dimensional beta-emission detectors.

12. A biochemical method for assay of a test medium, said test medium containing at least one potentially genotoxic agent, said test medium selected from the group consisting of aqueous chemical solutions, aqueous chemical mixtures, aqueous chemical suspensions, aqueous solutions under the influence of electromagnetic radiation, and aqueous solutions under the influence of particulate radiation, said method comprising at least the following steps:
(a) separately contacting living teleost embryos at the following three different developmental life-stages with said test-medium:
  (i) before mid-blastula transition;
  (ii) between midblastula transition and mid-gastrula stage;
  (iii) between midgastrula stage and the end of gastrulation,
(b) exposing said embryos to said test medium for a predetermined length of time,
(c) exposing said embryos to a chemical fixative,
(d) preparing said embryos for subsequent examination by a procedure which consists of the following steps:
  (i) removing the chorions of said embryos,
  (ii) removing the yolks of said embryos,
  (iii) contacting said embryos with a sequence of staining agents and destaining solutions to attach a plurality of labels to termini of fragmented strands of genomic DNA within said embryos, and
(e) examining said embryos by an optical technique for the residual presence of said labels, whereby the detection of said labels in said embryos is interpreted to indicate the action of at least one genotoxic agent in said test medium upon said embryos causing fragmentation of DNA.

13. A method as in claim 12 wherein steps (d)(ii) and (d)(iii) are inverted.

14. A method as in claim 12 wherein said embryos, after staining and destaining, are placed between two surfaces which are then sealed with an airtight seal to prevent drying of said embryos.

15. A method as in claim 12 wherein said embryos are obtained by combining eggs and sperm from female and male adults selected from the group consisting of wild-type members of any marine or freshwater teleost species, natural mutant members of any marine or freshwater teleost species, selectively bred mutant members of any marine or freshwater teleost species, and genetically-engineered mutant members of any marine or freshwater teleost species.

16. A method as in claim 12 wherein said embryos are obtained by combining eggs and sperm from female and male adults selected from the group consisting of wild-type members of the genus Danio, natural mutant members of the genus Danio, selectively bred mutant members of the genus Danio, and genetically-engineered mutant members of the genus Danio.

17. A method as in claim 12 wherein said embryos are parthenotes obtained by parthenogenetic activation of eggs from female adults selected from the group consisting of wild-type members of the genus Danio, natural mutant members of the genus Danio, selectively bred mutant members of the genus Danio, and genetically-engineered mutant members of the genus Danio.

18. A method as in claim 12 wherein said fixative is formaldehyde.

19. A method as in claim 12 wherein said label is selected from the group consisting of fluorescent nucleotide analogues, gold-conjugated nucleotide analogues, biotin-conjugated nucleotide analogues, digoxygenin-conjugated nucleotide analogues, and radioactive nucleotide analogues.

20. A method as in claim 12 wherein said label is covalently added to the 3'-termini of said fragmented DNA strands, by means of a terminal deoxynucleotidyl transferase enzyme.

21. A method as in claim 12 wherein said residual label is rendered detectable through binding to an antibody that is conjugated to a second label.

22. A method as in claim 14 wherein said surfaces are rigid, flat, and transparent.

23. A method as in claim 12 wherein said examination is performed with an instrument selected from the group consisting of brightfield microscopes, darkfield microscopes, phase-contrast microscopes, differential interference contrast microscoples, confocal epifluorescence microscopes, non-confocal epifluorescence microscopes, phosphorimagers, and two-dimensional beta-emission detectors.

24. A method of hierarchical testing, which is used to generate a quantitative and interpretive report on the frequencies of predefined cytological features and apoptotic nuclei in a teleost embryo exposed, or suspected of being exposed, to a genotoxic agent, said method comprising at minimum the following steps:

(a) exposing said embryo to a chemical fixative, (b) preparing said embryo for microscopic examination by a procedure consisting of the following steps:
  (i) removing the chorion,
  (ii) removing the yolk,
  (iii) contacting said embryo with a sequence of staining agents and destaining solutions which result in the labelling within said embryo of a plurality of cytological features selected from the group consisting of DNA, nuclei, apoptotic fragments of nuclei, chromosomes, chromatin- bound proteins, and chromosome-bound proteins, (c) generating a real-time image of the spatial distribution of said cytological features and apoptotic nuclei in said embryo, which are rendered detectable by virtue of said labelling, with a non-confocal epifluorescence microscope, (d) projecting said real-time image on a transparent sheet which is affixed to a video monitor, (e) repeatedly passing through all focal planes of said embryo, while recording, on said transparent sheet, by means of marking tools, the outlines of said labelled cytological features and apoptotic nuclei, (f) continuing process (e), under guidance from a human operator, until the outlines of substantially all of said cytological features and apoptotic nuclei are recorded on said transparent sheet, (g) computing the frequencies of said cytological features and apoptotic nuclei by statistical analysis of said outlines on said transparent sheet, (h) correlating said frequencies with the presence and efficacy of a genotoxic agent using an empirical database based on genotoxic standards.

* * * * *